United States Patent [19]

Marlett et al.

[11] Patent Number: 4,866,191
[45] Date of Patent: * Sep. 12, 1989

[54] STABILIZATION OF AMINE ALANES

[75] Inventors: Everett M. Marlett; Frederick W. Frey, both of Baton Rouge, La.; Steven W. Johnston, Seabrook, Tex.; Herbert D. Kaesz, Los Angeles, Calif.

[73] Assignee: Ethyl Corporation, Richmond, Va.

[ * ] Notice: The portion of the term of this patent subsequent to Mar. 8, 2005 has been disclaimed.

[21] Appl. No.: 211,831

[22] Filed: Jun. 27, 1988

Related U.S. Application Data

[63] Continuation-in-part of Ser. No. 133,141, Dec. 14, 1987, Pat. No. 4,782,171, which is a continuation-in-part of Ser. No. 51,720, May 20, 1987, Pat. No. 4,730,070.

[51] Int. Cl.$^4$ .............................................. C07F 5/06
[52] U.S. Cl. .................................................. 556/171
[58] Field of Search ......................................... 556/171

[56] References Cited

U.S. PATENT DOCUMENTS

| | | | |
|---|---|---|---|
| 2,680,059 | 6/1954 | Bragdon | 423/14 |
| 3,159,626 | 12/1964 | Ashley | 260/242 |
| 3,541,125 | 11/1970 | Sims | 260/448 |
| 3,642,853 | 2/1972 | Murib et al. | 260/448 |
| 3,926,833 | 12/1975 | Hoffman et al. | 252/188 |
| 4,006,095 | 2/1977 | Hoffman et al. | 252/188 |
| 4,456,584 | 6/1984 | Gautreaux | 423/644 |
| 4,474,743 | 10/1984 | Marlett | 423/347 |
| 4,528,176 | 7/1985 | Nelson | 423/644 |
| 4,730,070 | 3/1988 | Marlett et al. | 556/171 |
| 4,782,171 | 11/1988 | Marlett et al. | 556/171 |

OTHER PUBLICATIONS

Ruff et al., "J. Am. Chem. Soc.", 82, 2141 (1960).
Ashley, "Adv. Inorg. and Radiochem.", 8, 283 (1966).

*Primary Examiner*—Paul F. Shaver
*Attorney, Agent, or Firm*—P. M. Pippenger

[57] ABSTRACT

Process for retarding the decomposition of an amine alane, said process comprising contacting an amine alane which is substantially free of zirconium, hafnium, niobium, uranium, vanadium, and chromium, with an effective amount of a decomposition retarding agent selected from the class consisting of $O_2$, CO, nitrogen axides and alkyl nitrites.

10 Claims, No Drawings

STABILIZATION OF AMINE ALANES

CROSS-REFERENCE TO RELATED APPLICATIONS

This invention is a continuation-in-part of application Ser. No. 133,141, filed Dec. 14, 1987, now U.S. Pat. No. 4,782,171, which in turn is a continuation-in-part of application Ser. No. 051,720, filed May 20, 1987, now U.S. Pat. No. 4,730,070.

FIELD OF THE INVENTION

This invention pertains to the stabilization of amine alanes, $AlH_3NR_3$, wherein $NR_3$ is a tertiary amine.

In our aforementioned parent patent, U.S. Pat. No. 4,730,070, it is disclosed that amine alanes undergo decomposition by autocatalysis upon storage. The decomposition rate is slow at first, but can become rapid if allowed to proceed for a long enough period. The decomposition is catalyzed by titanium or a titanium-containing species. The mechanism of the decomposition, and the mechanism of titanium catalysis of the decomposition are not known.

In our parent patent, U.S. Pat. No. 4,730,070, we disclose and claim use of $O_2$, CO, nitrogen oxides, and alkyl nitrites to retard the decomposition of amine alanes that occurs when titanium or similar metal is present.

In this application and in parent application Ser. No. 133,141, supra we disclose that the aforementioned agents also retard decomposition of amine alanes when titanium or other similar metal is absent or substantially absent.

BACKGROUND OF THE INVENTION

U.S. Pat. No. 4,474,743 relates to silane preparation from amine alanes. It discloses that amine alanes can be prepared from $NaAlH_4$, that $NaAlH_4$ preparation from the elements is promoted by titanium, that amine alanes decompose on storage, and that the decomposition is catalyzed by titanium. It also discloses that the titanium-catalyzed decomposition can be combatted by recrystallizing the $NaAlH_4$ to remove titanium therefrom, or filtering the amine alanes product, in order to remove titanium from the amine alane.

Other art, U.S. Pat. Nos. 4,528,176, and 4,456,584 teaches that $NaAlH_4$ formation can be promoted by vanadium, zirconium and other metals.

SUMMARY OF THE INVENTION

In our above-stated patent, U.S. Pat. No. 4,730,070, we disclose that titanium-promoted decomposition of amine alanes can be retarded by passivating the titanium with $O_2$CO, nitrogen oxides, and alkyl nitrites. We also disclose that this passivation can be used in lieu of recrystallization of the $NaAlH_4$ or filtration of the amine alane, or as a "back up" to removal of the deleterious titanium by filtration.

The present invention is related to that disclosed in our parent application and parent patent, cited above. More specifically, the present invention relates to retardation of amine alane autodecomposition. In particular aspects, this invention pertains to retardation of amine alane autodecomposition that occurs when titanium or similar metal is absent or substantially absent. In another particular aspect, the present invention pertains to retarding the decomposition of amine alanes produced from recrystallized $NaAlH_4$. The recrystallization removes, or substantially removes, titanium or similar metal that is present with $NaAlH_4$, when that substance is formed in the presence of a promoter selected from titanium, zirconium, hafnium, niobium, uranium, vanadium, and chromium.

In a preferred embodiment, this invention comprises retardation of amine alane decomposition when said amine alane is produced from $NaAlH_4$ starting material which (1) contained vanadium, zirconium or chromium (or one or more compounds of these metals) used to promote formation of the $NaAlH_4$, and (2) was separated from the promoter material by recrystallization before the amine alane is produced. In another preferred embodiment, this invention can be used with amine alanes produced from $NaAlH_4$ made by a reactive system in which V, Zr and Cr were absent or substantially absent. This invention can also be extended to use with amine alanes stored in systems that are free or substantially free of vanadium zirconium or chromium.

It has been discovered that a decomposition retarding agent of this invention will retard the autodecomposition of an amine alane when added before or after the decomposition has begun.

DESCRIPTION OF PREFERRED EMBODIMENTS

This invention relates to retardation of autodecomposition of amine alanes. More particularly, it relates to slowing the rate of amine alane decomposition in the absence or substantial absence of a metal catalyst (e.g. Ti, Zr, Hf, Nb, U, V or Cr). In this invention, amine alane decomposition is delayed and/or slowed by use of $O_2$, CO, nitrogen oxides or alkyl nitrites.

One preferred embodiment of this invention comprises:

(a) preparation of $NaAlH_4$ by reacting Na, Al and $H_2$ in the presence of a promoter quantity of V, Zr, Hf, Nb, U, Cr or Ti, (b) recrystallizing the $NaAlH_4$ thereby produced to remove or substantially remove the promoter, (c) using the purified $NaAlH_4$ produced in (b) to prepare an amine alane, and (d) stabilizing the amine alane product by contacting it with a decomposition retarding amount of $O_2$, CO, nitrogen oxide or alkyl nitrite.

The heart of the invention is step (d).

The stabilization can be conducted, for example, using an amine alane which was not produced from $NaAlH_4$ prepared by a process promoted by the presence of Ti, Zr, Hf, Nb, U, Cr, or V. As mentioned above, the invention can be conducted when these metals are absent or substantially absent from the amine alane. Thus, this invention can be used to retard amine alane autodecomposition, and retard such decomposition which occurs in the substantial absence of one or more of the above-mentioned metals. As indicated above, in a preferred embodiment of this invention, a promoter metal is rendered absent or substantially absent by removing it via recrystallization of titanium-containing $NaAlH_4$ before the hydride is used to prepare the amine alane.

The titanium or other metal promoter can be removed in accordance with well-known recrystallization techniques, by dissolving the $NaAlH_4$ in a solvent in which it is soluble (and the promoter metal is substantially insoluble), filtering the solution, and then crystallizing the $NaAlH_4$ from the solution by evaporating solvent therefrom. Ethers such as dimethoxyethane and tetrahydrofuran are examples of solvents that can be used.

The reduction in the rate of amine alane decomposition can be obtained in two characteristic ways. First, the decomposition retarding agent can be contacted with the amine alane before the decomposition is noticeable. This retards the decomposition by delaying its onset. Second, the agent can be added after the decomposition is occurring to retard the decomposition by reducing its rate.

The invention is not limited by the time or more of addition of the decomposition rate reducing agent. Thus, the agent can be added more than once. Also, the retarding agent can be continuously or intermittently added; e.g. from the time the amine alane is formed and while the amine alane is stored prior to use. If desired, the reaction to prepare the amine alane can be conducted in the presence of a decomposition retarding agent, e.g. in a reaction zone in which CO is present, and thereafter; the presence of CO can be maintained during workup and storage of the amine alane. However, generally speaking, it is not necessary to introduce the decomposition retarding agent during amine alane preparation or workup, especially when recrystallized $NaAlH_4$ is used, and the amine alane is formed at ordinary reaction temperatures. Ordinarily, the decomposition rate of amine alane is not appreciable at these early stages, and therefore it is usually sufficient to introduce the decomposition retarding agent after the amine alane is isolated from the reaction mixture in which it was produced. Nonetheless, if the amine alane is deemed particularly sensitive to autodecomposition, it can be protected during its formation and isolation, as well as during its storage prior to use.

Although it is known that amine alanes undergo autodecomposition upon storage, the mechanism by which this decomposition occurs is not known. The rate of decomposition increases over time, and thus it appears that the decomposition may be catalyzed by an active species formed on decomposition. The active species is believed to contain aluminum. Although not bound by any theory, the retardation agents of this invention may act by slowing the formation of the active aluminum species, and/or by enhancing its transformation into a more inert species such as an aluminum oxide. The decomposition rate is dependent at least to some extent on the nature of the amine alane. N,N,N',N'-Tetra-methylethylenediamine (TMEDA) is a stronger ligand than tri-ethylamine ($Et_3N$), and should form a more stable adduct. The $AlH_3.TMEDA$ complex has been prepared and, indeed, proved to be more stable than $AlH_3.NEt_3$ on storage at room temperature and at 40° C. The decomposition rate tends to increase with temperature.

Various types of decomposition retarding agents are included in this invention. They include air, oxygen and oxides. Typically, the oxides are oxides of a nonmetallic element such as carbon or nitrogen. The preferred oxides are simple, or binary compounds; i.e., they are solely composed of oxygen and the nonmetallic element. Such compounds are exemplified by carbon monoxide and:

nitrous oxide: $N_2O$
nitric oxide: $NO$
nitrogen dioxide: $NO_2$
dinitrogen tetroxide: $N_2O_4$ This invention also includes use of organic nitrites as decomposition retarding agents. These have the formula RONO wherein R designates an organic radical, e.g. alkyl. It is believed that the exact structure and size of the organic radical is not critical. Lower alkyl nitrites (RONO), wherein R is an alkyl group of one to ten carbon atoms are preferred. Preferred compounds of this type include methyl-, ethyl-, propyl-, n-butyl-, isoamyl-, n-hexyl-, n-octyl-, and D-decylnitrite.

Through routine experimentation, a skilled practitioner can readily determine the desired amount of decomposition retarding agent required. For example, one can determine a lower limit below which the desired effect is not achieved. Also, one can also determine an upper limit of the amount of agent beyond which the agent causes no more retardation or an unwanted deleterious effect. Generally speaking, the decomposition retardation effect can be obtained when from 0.001 to 100 mole percent (based on the amount of amine alane to be stabilized) is admixed with the amine alane. Greater or lesser amounts can be used. A preferred range is from 0.01 to 50 mole percent.

The decomposition retarding agent can be contacted with the amine alane in any convenient manner. For example, when the agent is a gas, it may be added as a gas stream to the zone that contains the amine alane to be stabilized. When added in this way, not all of the retarding agent contacts the amine alane present. Therefore, one can use an excess of agent to insure that decomposition retardation takes place. The agents of this invention need not be added in pure form. For example, one or more agents can be mixed and added to the zone containing the amine alane to be stabilized. Also, the agent can be admixed, i.e. diluted with an inert material such as nitrogen or a noble gas, e.g. helium, argon, neon and the like, and then admitted to the zone containing the amine alane.

The process of this invention is preferably conducted under conditions which promote effective contact between the amine alane to be stabilized and the agent. For example, an inert liquid in which dissolved amine alane can be stirred, and a fine stream of gaseous decomposition retarding agent introduced into or over the stirred mixture. Countercurrent contacting of the mixture with the gas stream can also be used.

The temperature at which the process of this invention is conducted is not critical. Generally speaking, it is preferred to use a convenient reaction temperature at which the desired retardation takes place. Furthermore, low temperatures that are difficult to obtain in an economical manner, or at which the decomposition occurs at a tolerably slow rate, are undesired.

which are unnecessarily high, or at which some deleterious effect occurs are also undesireable. Generally speaking, the process of this invention can be conducted over a range of temperatures. A suitable temperature range is $-5°$ to about 70° C. and a preferred range is about 10° C. to about 60° C. The temperature selected depends to some extent on the method of use of the invention. Thus, one may treat the amine alane at any temperature in which it is not deleteriously affected by the agent. If the invention is used while the amine alane is being prepared, one uses the reaction temperature at which the amine alane synthesis is carried out, e.g. 0°–40° C. If the invention is used to stabilize amine alane after it is made, the temperature used is the temperature to which the amine alane product is exposed. The process can be conducted at atmospheric, sub-atmospheric or super-atmospheric pressures. In general, atmospheric pressure is suitable when using reactants that are liquids at reaction temperatures. A preferred pressure range is 0.2 to 10 atmospheres, more preferably 1 to 2 atmospheres.

EXAMPLE 1

An experiment was conducted to determine the thermal stability of $AlH_3 \cdot N(C_2H_5)_3$ treated with CO at 60.C.

In the experiment, the thermal stability of a toluene solution of the amine alane was determined by measurement of the hydrogen produced upon decomposition of the aluminum hydride, using a glass sample bulb connected to a Hg-filled gas buret. The sample bulb was made from a 25 mL round bottom flat the top of which was sealed to a ¼-inch Pyrex-to-Kovar join and equipped with a ¼-inch Swagelok tubing fitting. The buret was constructed from a 25 mL Pyrex buret having a bulb attached to the lower end by Tygon tubing. The upper end was sealed to a glass capillary line, which in turn was connected to the sample bulb by a matching Pyrex-to-Kovar seal and tubing fitting. Heat was supplied by a controlled temperature water bath (60° C.).

A solution of 0.23 g $AlCl_3$, 0.65 g triethylamine ($Et_3N$) and 3.85 g of dry toluene was prepared. To the solution was added 0.40 g of $NaAlH_4$, previously recrystallized from tetrahydrofuran. The mixture was stoppered and stirred overnight. The resultant solution (4.7 g, 4.3 wt. % $AlH_3$, 6.7 mmole) was filtered through a 0.45 micron Teflon filter into the aforementioned 25 mL flask.

Decomposition rates were calculated from the volume of $H_2$ collected (1.5 mmole per mmole $AlH_3$) relative to the amount of amine alane charged. Data was collected over time and yielded the following results.

| Elapsed Time (hr.) | Decomposition % |
|---|---|
| 3 | 0.13 |
| 22 | 0.20 |
| 48 | 0.42 |
| 72 | 0.83 |
| 96 | 4.56 |
| 99 | 5.65 |

The above results indicate that at 60° C., the decomposition of $AlH_3NEt_3$ was slow at first. The decomposition became autocatalytic after 72 hours, since in the time frame of 2–96 elapsed hours (4.56–0.83), or 3.73% by weight of the amine alane decomposed. In contrast, only 0.20% had decomposed in the first 22 hours, and at the end of 48 hours, only 0.42% had decomposed.

At 99 hours, ~20 mL of gaseous carbon monoxide was injected by syringe into the vapor space above the liquid in the sample bulb, and the bulb reconnected to the gas buret.

After 116 hours total elapsed time, 5.77% of the amine alane had decomposed; thus during the time frame of 99 to 116 hours, (5.77–5.65),or 0.12% of the amine alane had decomposed. At the end of 139 hours a total of 5.83% had decomposed. Thus in one time period 116-139 hours, an additional 0.06% decomposed. These results clearly indicate that CO slowed the rate of autodecomposition of the amine alane.

At the end of the test, the aluminum content of the toluene solution was analyzed. Assuming a 100% yield of the amine alane, analysis indicated 8.4% of it had been decomposed. This check was deemed fairly satisfactory.

Similar results in decomposition retardation are obtained when the amine alane is stabilized with 0.1 to 100 mole percent of CO, relative to moles of amine alane. Similar results are obtained when the CO is replaced with 0.01 to 1.0 mole (per mole of amine alane) of oxygen, either pure or in air, or when nitrous oxide, or other nitrogen oxide (e.g. NO, $NO_2$ or $N_2O_4$) or when methyl-, ethyl-, propyl-, n-butyl-, isoamyl-, n-hexyl-, n-octyl-, or n-decylnitrite is used as the decomposition retarding agent.

In a similar manner, it can also be shown that decomposition retardation can be obtained when the amine alane is substantially free of a metal selected from zirconium, hafnium, niobium, uranium, vanadium, and chromium, when the aforementioned decomposition retarding agents are employed.

EXAMPLE 2

An experiment similar to that reported in the above Example was conducted. For this experiment a solution was prepared of 0.23 g $AlCl_3$, 3.85 g of dry toluene, and 0.69 g of dry triethylamine. As before, these materials formed an almost clear, yellow solution. The solution was added to 0.34 g of $NaAlH_4$, recrystallized from tetrahydrofuran. The mixture (in a stoppered 50 mL flask) was stirred for five hours at room temperature. After that period, the solution was filtered through a Teflon filter of 0.45 microns and transferred to the 25 mL round bottom flask employed as a sample bulb in the previous Example. The bulb was fitted to the mercury-filled gas buret; and all lines were purged with nitrogen. Thereafter, about 20 mL of gaseous carbon monoxide was introduced into the flask with a syringe, and the flask tightly connected to the gas buret. The flask was immersed in a 60° C. water bath.

At the end of a 68 hour period, gas evolution indicated that only 0.20% of the amine alane had decomposed.

Similar results are obtained when the amine alane is stabilized with 0.01 to 1.0 mole of CO per mole of amine alane. Similar results are obtained when the CO is replaced with 0.01 to 1.0 mole (per mole of amine alane) of oxygen (either pure or in air), or when nitrous oxide, or other nitrogen oxide (e.g. NO, $NO_2$ or $N_2O_4$), or when methyl-, ethyl-, propyl-, n-butyl-, isoamyl-, n-hexyl-, D-octyl-, or n-decylnitrite is used as the decomposition retarding agent.

In a similar manner, it can also be shown that decomposition retardation can be obtained when the amine alane is substantially free of a promoter metal selected from zirconium, hafnium, niobium, uranium, vanadium, and chromium, when the aforementioned decomposition retarding agents are employed.

The procedure of the above Examples can be repeated at a temperature within the range of from $-5°$ C. to 70° C. The decomposition retarding effect of this invention can be obtained using amine alanes other than $AlH_3 \cdot N(Et)_3$. For example, the amine alanes can be prepared by using complexing tertiary amines other than triethylamine. Suitable complexing tertiary amines which may be utilized are liquids or low melting solids and include tertiary aryl, cycloalkyl, alkyl, alkenyl and aralkyl amines, including monoamines, diamines, triamines, etc. Typically, the amines may be N, N, N', N'-tetramethylethylenediamine, phenyldimethylamine, phenylmethylethylamine, tricyclohexylamine, or mixtures thereof, and other similar compounds. A more preferred class of amines for use in the invention are aliphatic tertiary amines, which include trialkylamine and trialkenylamine. Further, these amines may generally contain up to about 30 carbon atoms each, and preferably contain alkyl and alkenyl groups each having from 1 to about 10 carbon atoms. Thus, useful amines of this class are tri-D-butylamine; tri-sec-butylamine; dibutylpentylamine n-butyl-n-octyl-sec-butylamine; tripentylamine, exylamine; trihexenylamine; trioctadecylamine; didecenylpentylamine; tri-decenylamine; and the like, as well as mixtures thereof. A most preferred class of amines are those lower alkyl amines such as trimethylamine, N,N-dimethylethylamine, and particularly, triethylamine. By the term "lower" is meant that the alkyl groups each contain 6 carbon atoms or less.

Also usable complexing amines for forming amine alanes stabilized by this invention are the bicyclic amines quinuclidine, 1,4-diazabicyclo[2.2.2]octane; methyl-1,4diazabicyclo[2.2.2]octane, etc.

In view of the detailed description of this invention given above, a skilled practitioner can devise modifications or variations of the invention. Such modifications and variations are considered equivalents of this invention, and to be within the scope and spirit claims.

We claim:

1. Process for retarding the decomposition of an amine alane, said process comprising contacting an amine alane which is substantially free of zirconium, hafnium, niobium, uranium, vanadium, and chromium, with an effective amount of a decomposition retarding agent selected from the class consisting of $O_2$, CO, nitrogen oxides and alkyl nitrites.

2. The process of claim 1, wherein said agent is contacted with said amine alane prior to the onset of appreciable decomposition of said amine alane.

3. The process of claim 1 wherein said agent is contacted with said amine alane after the onset of appreciable decomposition of said amine alane.

4. The process of claim 2 wherein said agent is carbon monoxide.

5. The process of claim 3 wherein said agent is carbon monoxide.

6. The process of claim 1 being conducted at a temperature within the range of ambient temperature to about 70° C.

7. Process for retarding the autodecomposition of an amine alane, said process comprising contacting an amine alane with an effective amount of a decomposition retarding agent selected from the class consisting of $O_2$, CO, nitrogen oxides and alkyl nitrites.

8. The process of claim 7 wherein said decomposition retarding agent is carbon monoxide.

9. A process for stabilizing an amine alane product, said process comprising
   (a) preparing of $NaAlH_4$ by reacting Na, Al and $H_2$ in the presence of a promoter quantity of V, Zr, Hf, Nb, U, Cr or Ti,
   (b) recrystallizing the $NaAlH_4$ thereby produced to remove or substantially remove the promoter,
   (c) using the purified $NaAlH_4$ produced in (b) to prepare an amine alane, and
   (d) stabilizing the amine alane product by contacting it with a decomposition retarding amount of $O_2$, CO, nitrogen oxide or alkyl nitrite.

10. The process of claim 9 wherein said decomposition retarding agent is carbon monoxide.

* * * * *